(12) United States Patent
Ou et al.

(10) Patent No.: US 10,226,719 B2
(45) Date of Patent: Mar. 12, 2019

(54) ADSORPTIVE SEPARATION OF MULTI-COMPONENT FLUID MIXTURES

(71) Applicant: ExxonMobil Chemical Patents Inc., Baytown, TX (US)

(72) Inventors: John D. Y. Ou, Houston, TX (US); Stephen A. Baehl, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 14 days.

(21) Appl. No.: 15/503,556

(22) PCT Filed: Aug. 14, 2015

(86) PCT No.: PCT/US2015/045270
§ 371 (c)(1),
(2) Date: Feb. 13, 2017

(87) PCT Pub. No.: WO2016/053484
PCT Pub. Date: Apr. 7, 2016

(65) Prior Publication Data
US 2017/0239591 A1    Aug. 24, 2017

Related U.S. Application Data

(60) Provisional application No. 62/057,886, filed on Sep. 30, 2014.

(51) Int. Cl.
*C07C 7/12* (2006.01)
*C07C 7/13* (2006.01)
*B01D 15/18* (2006.01)

(52) U.S. Cl.
CPC ............ *B01D 15/1828* (2013.01); *C07C 7/12* (2013.01); *C07C 7/13* (2013.01)

(58) Field of Classification Search
None
See application file for complete search history.

(56) References Cited

U.S. PATENT DOCUMENTS 2,985,589 A   5/1961   Broughton et al.
3,040,777 A   6/1962   Carson et al.
(Continued)

FOREIGN PATENT DOCUMENTS

| CN | 104056467 | 9/2014 |
| DE | 10011736 | 9/2001 |
| WO | 2013/055932 | 4/2013 |

OTHER PUBLICATIONS

Jo, Se-Hee et al., "The Comparative Analysis of Single-Cascade Five-Zone and Two-Zone SMB Systems for the Separation of a Ternary Amino Acid Mixture," The Canadian Journal of Chemical Engineering, vol. 85, No. 6, Dec. 19, 2007, pp. 874-882.
(Continued)

*Primary Examiner* — Tam M Nguyen

(57) ABSTRACT

An adsorptive separation process and system are used for separation of multi-component fluid mixtures. The separation process and system may include establishing, in a fluid flow within the system, a concentration distribution of the fluid mixture components based upon the components' relative affinities to the adsorbent. The concentration distribution could be establishing using a simulated moving bed system, wherein it is possible to maintain separately-identifiable portions of the fluid flow, respectively rich in strongly-adsorbing, intermediately-adsorbing, and weakly-adsorbing compounds of the fluid mixture. An intermediate raffinate of high purity in the intermediately-adsorbing compound is directly withdrawn from the portion of the fluid flow rich in intermediately-adsorbing compound(s), providing a single-stage adsorptive separation of a compound having intermediate affinity to the adsorbent. The portion of
(Continued)

the fluid flow rich in intermediately-adsorbing compound(s) may be established directly upstream from the point of fluid mixture feed injection into the fluid flow.

12 Claims, 5 Drawing Sheets

(56) References Cited

U.S. PATENT DOCUMENTS

| | | | |
|---|---|---|---|
| 3,192,954 A | 7/1965 | Gerhold et al. | |
| 3,422,848 A | 1/1969 | Liebman et al. | |
| 3,706,812 A | 12/1972 | Derosset et al. | |
| 4,029,717 A | 6/1977 | Healy et al. | |
| 4,313,015 A | 1/1982 | Broughton | |
| 4,402,832 A | 9/1983 | Gerhold | |
| 4,478,721 A | 10/1984 | Gerhold | |
| 5,114,590 A | 5/1992 | Hotier et al. | |
| 5,405,534 A | 4/1995 | Ishida et al. | |
| 6,759,563 B1* | 7/2004 | Hibbs | C07C 5/2791 585/734 |
| 7,202,205 B1* | 4/2007 | Connor | C11D 1/146 510/505 |
| 7,837,881 B2 | 11/2010 | Aumann et al. | |
| 7,915,471 B2* | 3/2011 | Leflaive | C07C 5/2737 585/477 |
| 7,977,526 B2 | 7/2011 | Porter | |
| 8,168,845 B2 | 5/2012 | Porter et al. | |
| 8,404,916 B1* | 3/2013 | Pieper | C07C 7/12 585/820 |
| 2002/0055665 A1* | 5/2002 | Pavone | C07C 7/005 585/825 |
| 2010/0116639 A1* | 5/2010 | Park | B01D 3/143 203/4 |
| 2010/0125162 A1* | 5/2010 | Noe | C07C 7/12 585/822 |

OTHER PUBLICATIONS

Mun, Sungyong, "Effect of a Partial-Feeding Application on Product Purities and Throughput of a Five-Zone Simulated Moving Bed Process for the Separation of a Ternary Nucleoside Mixture ," Process Biochemistry, Elsevier, NL, vol. 46, No. 4, Jan. 10, 2011, pp. 977-986.

Kroschwitz, J. L., Editor, "Simulated Moving-Bed Operation", Encyclopedia of Chemical Technology, 4th Edition, 1991, vol. 1, pp. 582-583.

Kroschwitz, J. L., Editor, "Modeling of UOP Sorbex Systems", Encyclopedia of Chemical Technology, 4th Edition, 1991, vol. 1, pp. 583-596.

* cited by examiner

ADSORPTIVE SEPARATION OF MULTI-COMPONENT FLUID MIXTURES

CROSS-REFERENCE TO RELATED APPLICATION

This application is a U.S. National Stage application that claims the benefit of and priority to PCT/US2015/045270, filed Aug. 14, 2015 and U.S. Provisional Patent Application No. 62/057,886, filed Sep. 30, 2014, the disclosures of which are incorporated herein by reference in their entirety.

FIELD OF THE INVENTION

This invention relates to a process for separating one or more of the components from a multicomponent fluid mixture. More particularly, this invention relates to a process to for separating organic compounds from such a fluid mixture by means of adsorption apparatus, such as moving-bed or simulated moving-bed adsorption apparatus, and a system comprising such apparatus.

BACKGROUND OF THE INVENTION

Various means are currently available to separate the components of a multicomponent fluid mixture. For instance, distillation and/or fractionation are frequently used to separate components with different boiling points. However, some fluid mixtures comprise components which have similar boiling points, and in such cases, separation by distillation may be a difficult and an inefficient means to separate these components. Too many contaminants, e. g., unwanted components, also may evaporate along with (or fail to evaporate from) the desired component(s), or the separation may require high energy expenditures due to the recycling through the distillation process that may be necessary to attain a desired degree of separation or purity.

Consequently, adsorption is often preferred as a process for separating components from a multicomponent fluid mixture to obtain relatively pure products, particularly where the components have similar boiling points. In an adsorption process, separation of the fluid components is accomplished because the adsorbent solid material has a physical and/or chemical attraction for one or more of the components of the mixture in preference to other components of the mixture. Although all of the components of a mixture may be attracted in varying degrees to the material, there is a preference engineered into the process, such that predominantly the desired component(s) may be attracted and remain with the material in preference over all others. For instance, polarity of adsorbent and mixture components is frequently used as a means for engineering the adsorptive preference, or relative adsorptivity, into the process. Thus, a hypothetical mixture could comprise two compounds, a polar compound A and a non- or less-polar compound B. Thus, A would have a greater affinity for a polar solid adsorbent than B (and the opposite would be true for a non-polar solid adsorbent).

Although adsorption could be practiced by passing this A-B fluid mixture over a fixed bed of solid adsorbent (allowing A to adsorb and B to remain in the fluid flowing over the adsorbent), a more efficient technique would involve the continuous countercurrent movement of the adsorbent and the fluid mixture. Such a technique is often referred to as a theoretical moving bed (TMB) process. The efficiency can be appreciated by envisioning a single column with (i) downwardly-flowing fluid comprising the hypothetical A-B fluid mixture, and (ii) upwardly-flowing solid adsorbent. A fluid inlet delivers the A-B fluid stream into the column at a point midway between the top and bottom of the column. The A, being polar, is adsorbed by the polar adsorbent and is thereupon carried toward the top of the column, while the apolar B remains in the fluid, flowing down the column. Thus, it can be seen that a relatively short column can quickly achieve a separation that, with stationary adsorbent and downward fluid flow only, might take a substantially longer time. In addition, the column can conveniently be run in a continuous manner by drawing off the fluid, comprising B and substantially no A, from the bottom of the column. Such a stream may be labeled a "raffinate stream" and can be drawn off via a transfer line from the bottom of the column. At the top of the column, a desorbent may be injected by another transfer line, in order to solvate the A from the adsorbent, allowing the desorbent-and-A fluid mixture to be drawn off the top of the column as an "extract stream" carried in an overhead transfer line from a point below the point of desorbent entry, but above the feed entry. Further, the (now-empty) adsorbent may be returned to the bottom of the column via a recycle stream, and the process allowed to run continuously. See, for example, discussion in Kirk-Othmer Encyclopedia of Chemical Technology, Fourth Edition (1991), Vol. 1, at page 582-583 & FIG. 7, which is incorporated herein by reference.

Of course, achieving movement of a solid adsorbent is at best prohibitively difficult in practice. However, the countercurrent flow of a solid adsorbent may be simulated without actually moving the adsorbent—a chief example of which is the so-called "simulated moving bed" (SMB) process. See, for instance, U.S. Pat. Nos. 2,985,589, 4,029,717, 4,402,832, and 4,478,721, as well as Kirk-Othmer Encyclopedia of Chemical Technology, Fourth Edition (1991), Vol. 1, pages 583-596, each of which is incorporated herein by reference. Such processes have been developed for the separation of p-xylene from a mixture of $C_8$ aromatics (UOP Parex™), n-paraffin separation (UOP Molex™), and olefin-paraffin separation (UOP Olex™). Variants have been developed, such as the Toray Aromax™ process for p-xylene separation.

In general, SMB processes involve holding the adsorbent stationary while periodically carrying out the simultaneous downstream advancement of all injection and withdrawal points along the adsorbent system, thereby simulating the upstream (counter-current) "flow" of the stationary solid adsorbent.

The concept may be illustrated by envisioning the following modifications to the previously-described TMB column illustrating separation of A and B. Not counting the theoretical adsorbent recycle stream, the previously-described TMB column is coupled to the following four streams carried in four transfer lines, from top to bottom of the column: (1) an inlet desorbent stream delivered in a first transfer line to the top of the column; (2) an outlet extract stream withdrawn in a second transfer line, just below the desorbent inlet; (3) an inlet feed stream delivered in a third transfer line to the middle of the column; and (4) an outlet raffinate stream withdrawn in a fourth transfer line from the bottom of the column. In the previously-described theoretical moving bed column, each of these four streams remained continuously carried through each of the four stationary transfer lines, while the fluid in the column flowed down through the column (i.e., downward relative to the stationary transfer lines), and the theoretical adsorbent flowed up through the column (i.e., upward relative to the stationary transfer lines). SMB takes advantage of the fact that the same relative motion of the adsorbent (e.g., flowing up through the column) may be obtained by holding the adsorbent stationary while moving the four transfer lines in a downward (e.g., downstream with respect to the flowing fluid) direction. Of course, continuous movement of the transfer lines would be impractical, but periodic simultaneous downward shifting of all transfer lines approximates the same effect.

While this process could in theory be carried out continuously by simple downstream motion on a column of infinite height, this cannot be accomplished in practice. However, the same continuous effect can be achieved by recycling the downward-flowing fluid to the top of the column (allowing the fluid to circulate continually in the same direction through the column), and recycling the motion of the transfer lines such that, when the bottom-most transfer line (e.g., the fourth transfer line in the above illustration) reaches the bottom of the column, it is moved to the top of the column, while the other three transfer lines are simultaneously moved down. The next transfer line (e.g., the third line in the above illustration) is now at the bottom, and at the next movement of the transfer lines, it will move to the top, while the fourth transfer line is correspondingly moved down. It can be seen, then, that the sequence of transfer lines remains constant, even while all the lines are moved along the column. Thus, the sequence of streams carried in those lines likewise remains constant (desorbent inlet-extract withdrawal-feed inlet-raffinate withdrawal, repeating).

Yet, moving transfer lines along a column is itself also difficult in practice. A simpler method involves leaving the transfer lines in place, while sequentially redirecting the fluid streams to the next successive transfer line. This can be accomplished, e.g., by a rotary valve or like device coupled to all four transfer lines connected to the column. See, for instance, U.S. Pat. Nos. 3,040,777, 3,192,954, and 8,168,845, each of which is incorporated herein by reference. The rotary valve is additionally coupled to four other process lines, two of which continuously carry the fluid feed stream and the desorbent stream to the valve, and two of which continuously carry the extract and raffinate streams from the valve. The rotary valve functions on the same principles as a multi-port stopcock, routing the streams (in the order desorbent-extract-feed-raffinate) to and from, as applicable, each of the four transfer lines coupled to the column. The rotary valve may periodically rotate its position, thereby advancing each stream to the next successive transfer line coupled to the column. Further, more than four transfer lines may be used; for instance, 12 transfer lines could be employed, such that two empty transfer lines are between each stream-carrying transfer line at any given time. Each successive shift of the rotary valve would direct each stream to the next successive transfer line.

As is illustrated above, conventional adsorptive separations such as SMB are typically best directed at binary separations (that is, separation of a feedstream into two outlet streams). Thus, conventional approaches employ multiple-step separation to deal with mixtures comprising three or more compounds, each of which is to be separated. That is, in a mixture comprising (in decreasing order of affinity to a polar adsorbent, i.e., most- to least-polar) compounds A, B, and C, a first step would involve separation of polar A from less polar B and C, and a second step would thereafter be necessary to separate the more polar B from less polar C. This separation process can be excessively complex, particularly where the compound of interest is the intermediately-adsorbing B, which cannot easily be cut away from the rest of the mixture in a binary separation. For example, this problem complicates the separation of olefins from complex mixtures such as naphtha and/or the distillate streams from thermal cracking processes such as steam cracking, coking, visbreaking, and the like. Such streams typically contain, in order of increasing affinity to polar solvents or adsorbents, paraffins, olefins, aromatics, and hetero-compounds (wherein the order would be reversed with respect to non-polar solvents or adsorbents). Thus, a conventional simulated countercurrent adsorptive separation would require at least two steps to separate the olefins from such a mixture. A simple single-step adsorptive separation of olefins (or any other intermediately adsorbed compound) from complex mixtures would significantly enhance efficiency of the desired separation.

SUMMARY OF THE INVENTION

According to the present invention, systems, apparatus, and methods employing the same are provided for adsorptive separation of multi-component (i.e., three or more component) fluid mixtures. In particular, an intermediately-adsorbing compound is separated from the fluid mixture in a single adsorption separation step, thereby obviating the need to use multiple adsorptions in series to separate the intermediately-adsorbing compound.

A process according to some aspects includes establishing a concentration distribution of compounds in a fluid mixture, the distribution being based upon the compounds' relative affinity to an adsorbent in a moving bed, simulated moving bed, or other adsorptive separation system. In certain aspects, the established concentration distribution approximates a chromatographic separation (e.g., by using polar or non-polar adsorbent to establish a distribution based on increasing affinity to the polar or non-polar adsorbent). The fluid mixture comprises at least weakly-adsorbing compound(s), intermediately-adsorbing compound(s), and strongly-adsorbing compound(s).

Upon establishment of the concentration distribution, an intermediate raffinate comprising the intermediately-adsorbing compound is drawn off from the system at a point where the concentration distribution is such that the fluid in the system is rich in the intermediately-adsorbing compound and depleted in the weakly- and strongly-adsorbing compounds. An additional raffinate stream and an extract stream may also be drawn off to recover weakly-adsorbing and strongly-adsorbing compounds, respectively, at points along the concentration distribution rich in those respective compounds.

In certain aspects, the concentration distribution is established using an adsorption system employing a countercurrent or simulated countercurrent flow of the fluid mixture and solid adsorbent, such as a simulated moving bed (SMB) system. The adsorption system includes an adsorbent chamber comprising adsorbent disposed therein, or a plurality of adsorbent chambers each comprising adsorbent disposed therein and each arranged in serial fluid communication. In either configuration, the adsorbent system comprises a recycle line connecting a downstream end of the system to an upstream end of the system, enabling fluid in the system to circulate by flowing continuously in the same downstream direction through the chamber or chambers, then back up to the upstream end of the system via the external recycle line. Such fluid circulating through the system is referred to herein as a "continuous downstream fluid flow" in the system. As used herein, "downstream" and "upstream," unless indicated otherwise, each are used with respect to the fluid flow in the adsorbent system.

Two inlet streams are provided to the continuous downstream fluid flow in the system, and three withdrawal streams are removed from the continuous downstream fluid flow in the system, in the following order (listed from upstream to downstream with respect to the continuous downstream fluid flow):

(i) a fluid mixture feed stream comprising the weakly-, intermediately- and strongly-adsorbing compounds is introduced to the continuous downstream fluid flow;

(ii) a raffinate withdrawal stream comprising the weakly-adsorbing compound(s) is withdrawn from the continuous fluid flow;

(iii) a desorbent stream comprising desorbent is introduced to the continuous downstream fluid flow;

(iv) an extract withdrawal stream comprising strongly-adsorbing compound(s) is withdrawn from the continuous downstream fluid flow; and (v) an intermediate raffinate withdrawal stream comprising the intermediately-adsorbing compound(s) is withdrawn from the continuous downstream fluid flow.

Processes and systems according to particular aspects consist or consist essentially of the aforementioned streams. Further, in some aspects, each of the aforementioned streams is directly upstream of the subsequent stream (i.e., the fluid mixture feed stream is directly upstream of the raffinate withdrawal stream, and so on). In addition, given the circulating nature of the continuous downstream fluid flow, the above-listed sequence of streams is repeating with respect to the fluid flowing in the system (that is, the intermediate raffinate withdrawal stream is directly upstream of the fluid mixture feed stream). When one stream is "directly upstream" or "directly downstream" of another, as used herein, it is meant that none of the other above-listed injection or withdrawal streams are introduced to (or withdrawn from) the fluid flow between the two referenced streams.

DETAILED DESCRIPTION OF THE EMBODIMENTS

Figure 1:
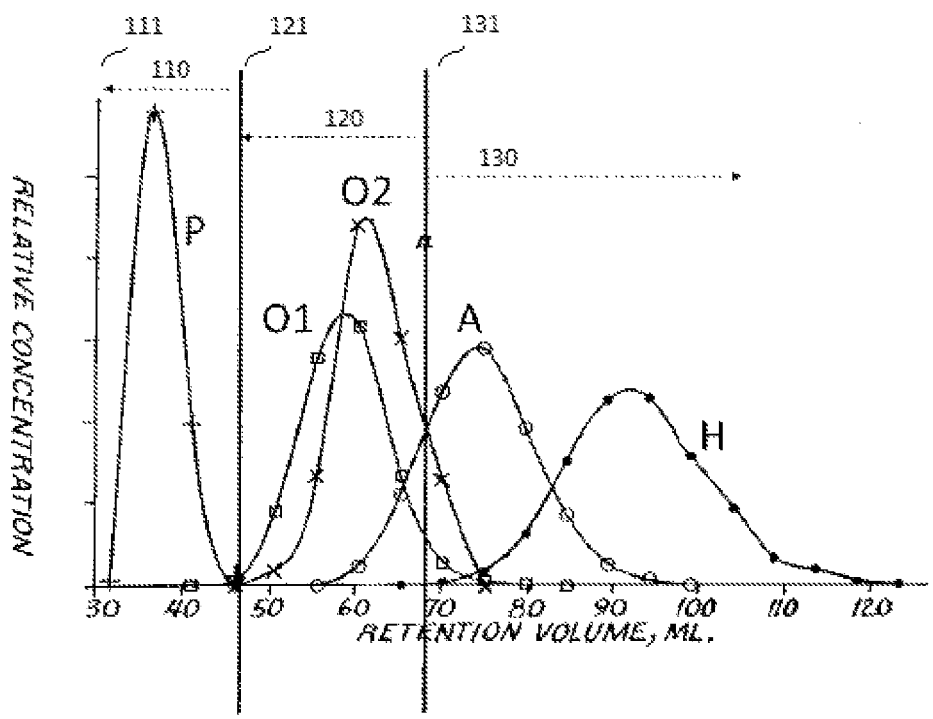
FIG. 1 is a chart illustrating relative concentrations at various retention volumes of components of a fluid mixture in a chromatographic separation.

The present invention describes processes, systems, and apparatus for the adsorptive separation of a mixture of three or more compounds in which each compound has a different affinity for the adsorbent. For instance, some aspects involve the separation of a mixture comprising at least a weakly-adsorbing compound, an intermediately-adsorbing compound, and a strongly-adsorbing compound. Particular aspects include separation of the intermediately-adsorbing compound from a mixture comprising that compound and both weaker- and stronger-adsorbing compounds. Examples of such aspects include separation of olefins from a mixture comprising, in increasing order of affinity to adsorbent (e.g., to a polar adsorbent): paraffins, olefins, aromatics, and hetero-compounds (wherein the order would be reversed with respect to non-polar adsorbents).

Other aspects of the present invention may involve separation of any other intermediately-adsorbing compound. For instance, such aspects may include separation of an intermediately-adsorbing compound from a $C_8$ aromatics fluid mixture (such as ethylbenzene), wherein strongly-adsorbing para-xylene and weakly-adsorbing ortho- and meta-xylenes may also be drawn off, respectively (the weak and strong adsorptive qualities being based upon, e.g., a non-polar adsorbent, and being reversed where polar adsorbent is used). Further, other aspects of separations of any suitable mixture may be based upon affinities to adsorbents based upon criteria instead of or in addition to polarity (e.g., molecular size).

Concentration Distribution

Accordingly, a process of some embodiments includes establishing a concentration distribution of compounds in a fluid mixture, the distribution being based upon the compounds' relative affinity to an adsorbent. The established concentration distribution may approximate a chromatographic separation (e.g., by using polar or non-polar adsorbent to establish a distribution based on increasing and/or decreasing affinity to the polar or non-polar adsorbent). As will be described in more detail below, the concentration distribution in particular embodiments is established in a continuous downstream fluid flow within a simulated moving bed or like system.

An intermediate raffinate stream comprising the intermediately-adsorbing compound may be drawn off from the continuous downstream fluid flow in the system at a point where the flowing fluid is rich in the intermediately-adsorbing compound and depleted in other species. In addition, a raffinate withdrawal stream and an extract withdrawal stream may also be drawn off to recover weakly-adsorbing and strongly-adsorbing compounds, respectively, at points in the fluid flow rich in those respective compounds. In other embodiments, the process may be simplified by forcing the weakly-adsorbing compound(s) into the extract stream along with the strongly-adsorbing compounds, thereby eliminating the necessity of a raffinate stream in addition to the intermediate raffinate stream. Such embodiments are useful where there is no need to separate the strongly-adsorbing and weakly-adsorbing compounds from each other, while still preserving the ability to obtain the relatively pure intermediately-adsorbing compound in a single adsorptive separation process (rather than multiple processes run in series).

As used herein, a portion of fluid (or fluid flow) is "rich," "rich in," or "enriched" in a specified one of the weakly-adsorbing compound(s), intermediately-adsorbing compound(s), and strongly-adsorbing compound(s) when that specified one of those compounds is present in the portion of fluid at a greater concentration relative to that compound's concentration in the fluid mixture feed, on the basis of the combined weakly-, intermediately-, and strongly-adsorbing compounds (e.g., having higher wt %, mol %, or the like, on the basis of combined weight (or moles, etc.) of weakly-, intermediately-, and strongly-adsorbing compounds). When a portion of fluid is described as being "depleted" in a specified one of the weakly-adsorbing compound(s), intermediately-adsorbing compound(s), and strongly-adsorbing compound(s), it is meant that the concentration of that specified one of those compounds is present in the portion of the fluid in lower concentration relative to that compound's concentration in the fluid mixture feed, on the basis of the combined weakly-, intermediately-, and strongly-adsorbing compounds. In other words, the comparison intended with "rich," "depleted," and the like, when referencing any one or more of the weakly-, intermediately-, and strongly-adsorbing compounds, is among the weakly-, intermediately-, and strongly-adsorbing compounds, disregarding other constituents of a referenced fluid (e.g., desorbent). Thus, a fluid portion comprising 15 wt % of an intermediately-adsorbing compound, 1 wt % combined of weakly- and strongly-adsorbing compounds, and 84 wt % desorbent, would still be considered "rich in" the intermediately-adsorbing compound where the fluid mixture feed comprises approximately equal parts (i.e., about 33.33 wt %) each of the weakly-, intermediately-, and strongly-adsorbing compounds, because that fluid portion is more concentrated than the fluid mixture in intermediately-adsorbing compound, relative to the weakly- and strongly-adsorbing compounds.

On the other hand, where a fluid (or stream) is described as being "depleted in" desorbent relative to another fluid (or stream), this simply means that the wt % or mol % of the desorbent in the fluid (or stream) is less than the wt % or mol % of the desorbent in the other fluid (or stream), on the basis of the entire contents of the referenced fluids or streams.

FIG. 1 provides a visual approximation of a separations procedure according to to some embodiments, based upon establishing a chromatographic concentration distribution of a mixture including paraffins (P), olefins (O1 and O2), aromatics (A), and hetero-compounds (H). In particular, FIG. 1 is a chart of relative concentration of each of the aforementioned compounds at various retention volumes (retention volume being the product of retention time and fluid flow rate in a chromatography column, thereby normalizing the concentration distribution against various fluid flow rates). Although the chart displays a chromatographic separation of the compounds in a small-scale chromatography column, it provides a convenient visual demonstration of the concepts underlying the establishment of a concentration distribution in a separations system according to various aspects of the present invention. In particular, a similar concentration distribution to that shown in FIG. 1 can be established on a larger scale in a SMB or other like system according to some aspects of the present invention. At a very high level, the concentration distribution may be established by taking advantage of the relative affinities of the different compounds for the adsorbent in the system; the greater the affinity, the slower the compound moves through the system. The simulated countercurrent flow of adsorbent in a SMB system (noted previously and discussed in greater detail below) may enhance this effect, even to the point of giving net upstream flow (relative to flow of the fluid mixture in the system) to some of the more strongly-adsorbing compounds of the mixture. As depicted in FIG. 1, the higher retention volume corresponds to greater affinity; so, the right side of the chart represents an upstream end, and the left side a downstream end, of a concentration distribution in a SMB system, relative to fluid flow in the system.

Figure 2:
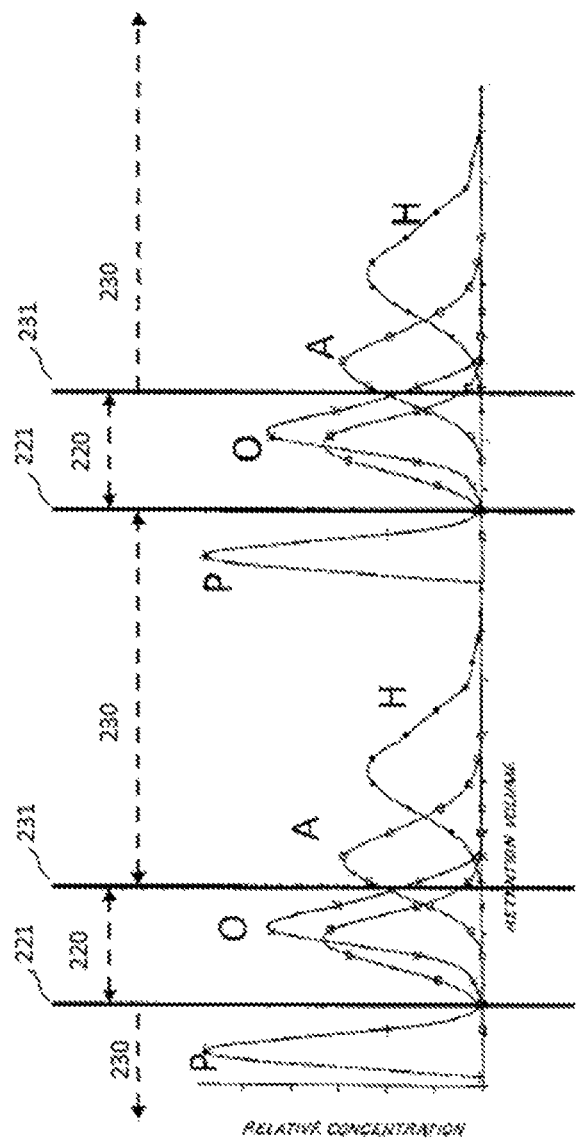
FIG. 2 is a stylized chart illustrating a chromatographic concentration profile established in a system employing continuous downstream fluid flow.

The three cuts (raffinate cut 110, intermediate raffinate cut 120, and extract cut 131) at the chromatographically-separated mixture shown in FIG. 1 illustrate how the system may be designed to include placement of the raffinate withdrawal stream, intermediate raffinate withdrawal stream, and extract withdrawal stream, respectively, at points 111, 121, and 131 along the concentration distribution established in the SMB or like system. Further, it should be noted that placement of the cuts could of course be altered based upon purity requirements. For instance, the intermediate raffinate cut 115 could be narrowed by moving the extract stream withdrawal point 131 to the left on the chart (that is, downstream in a corresponding separations system) to increase purity of the olefins at the cost of reduced per-pass recovery.

Where the fluid is allowed to flow through a separations system in a continuous downstream fluid flow (due, e.g., to an external recycle loop conveying the fluid from a downstream end of the system back to the upstream end), while maintaining the established to concentration distribution, it will be appreciated that the relative concentration curve of FIG. 1 would repeat continuously, as depicted in FIG. 2. This further demonstrates how a procedure according to some embodiments may be implemented, in which both the weakly-adsorbing paraffins and the strongly-adsorbing aromatics/hetero-compounds are drawn off in a single extract cut (230), while the intermediately-adsorbing olefins are drawn off in a single raffinate cut (220), accomplished by, e.g., removal of the raffinate withdrawal stream 111 from FIG. 1, leaving only intermediate raffinate withdrawal stream 221 and extract withdrawal stream 231 in FIG. 2.

Continuous Countercurrent Adsorption Zones

According to some embodiments, the above-described techniques involving creating and/or maintaining concentration distributions may be implemented in a continuous countercurrent adsorption system, such as a SMB system. As noted previously, SMB simulates a continuous countercurrent flow of solid adsorbent and fluid mixture.

Figure 3:
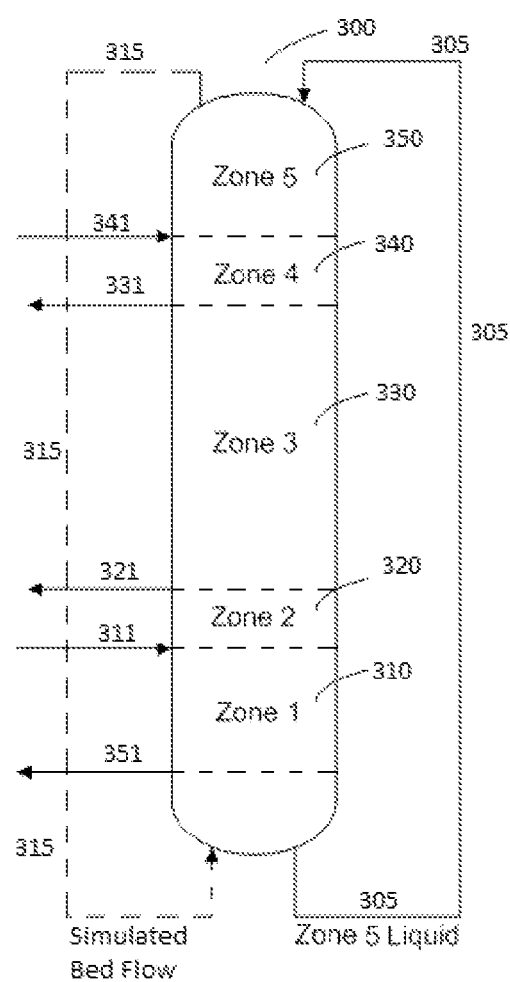
FIG. 3 is a schematic illustrating a continuous countercurrent flow adsorption process according to some aspects of the present invention.
Figure 4:
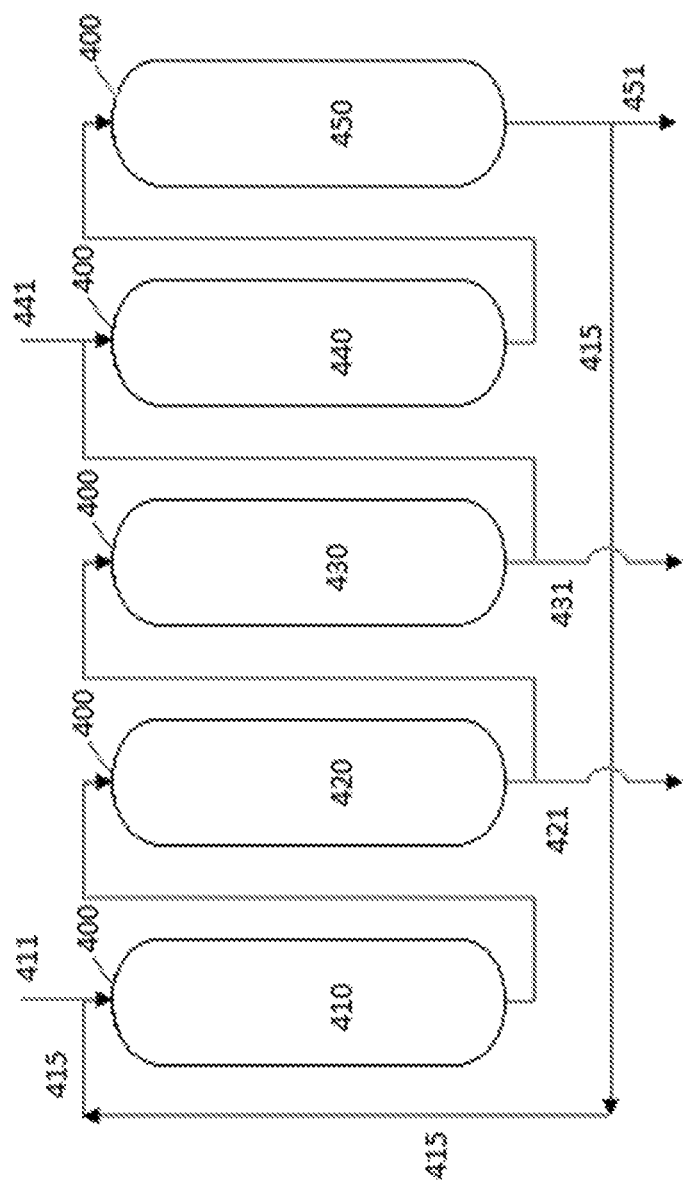
FIG. 4 is a schematic illustrating a multi-chamber continuous countercurrent flow adsorption process according to other aspects of the present invention.

FIG. 3 is a conceptual schematic of continuous countercurrent flow adsorption processes according to some aspects of the present invention. For purposes of simplicity, FIG. 3 illustrates a process as carried out in an adsorption system comprising a single vertical adsorbent chamber [300] packed with adsorbent solids (not shown). The packed adsorbent solids may be present in the chamber in various aspects in packing, or in one or more trays and/or beds stacked within the chamber. In certain embodiments, the adsorbent may be present in a plurality of beds structurally separated from one another within the chamber 300 by horizontal liquid collection/distribution grids, each grid being connected to a transfer line defining a transfer point at which process streams may enter and leave the vertical adsorption chamber 300. It will also be understood that an adsorption system could instead comprise a plurality of adsorbent chambers 400 in serial fluid communication, as illustrated in FIG. 4, each chamber comprising adsorbent solids as packing, stacked trays, and/or stacked beds (not shown). Further, because the figures are, of course, stationary, reference will be made to "simulated adsorbent flow," "simulated counter-current flow," and the like, by which it should be understood that such simulated flow is achieved according to conventional SMB techniques as described previously, such as by the movement of the various feed and outlet transfer lines in the direction of fluid flow in the adsorption chamber 300, or by re-routing the various inlet and outlet streams simultaneously to progressively farther downstream (and fixed) transfer lines. For the sake of simplicity, FIG. 3 shows only five transfer lines conveying the various inlet and outlet streams 311, 321, 331, 341, and 351. However, it will be understood that, in accordance with the previous description of SMB systems, multiple other transfer lines (not shown in FIG. 3) may be disposed along an adsorbent chamber or chambers, and a rotary valve or other like device used to re-route each stream to the next successive line. With such movement together and at regular intervals, the adsorbent bed(s) may thereby be said to "move" relative to (and in a direction opposite to the motion of) the inlet and withdrawal streams. The chamber 300 further includes a recycle conduit 305 coupling the bottom portion of the chamber 300 to the top portion of the chamber 300, thereby enabling maintenance of a continuous downstream fluid flow through the system, involving fluid flow down through the chamber 300 before being externally circulated back up to the top of the chamber 300 through the recycle conduit 305, at which point it flows back down through the chamber 300.

In embodiments according to the illustration of FIG. 3, two inlet streams are provided to the continuous downstream fluid flow in the system, and three withdrawal streams are removed from the continuous downstream fluid flow in the system, in the following order (listed from upstream to downstream with respect to the continuous downstream fluid flow):

(i) a fluid mixture feed stream 311 comprising the weakly-, intermediately- and strongly-adsorbing compounds is introduced to the continuous downstream fluid flow;

(ii) a raffinate withdrawal stream 351 comprising the weakly-adsorbing compound(s) is withdrawn from the continuous fluid flow;

(iii) a desorbent stream 341 comprising desorbent is introduced to the continuous downstream fluid flow;

(iv) an extract withdrawal stream 331 comprising strongly-adsorbing compound(s) is withdrawn from the continuous downstream fluid flow; and (v) an intermediate raffinate withdrawal stream 321 comprising the interemediately-adsorbing compound(s) is withdrawn from the continuous downstream fluid flow.

Furthermore, five zones 310, 320, 330, 340, and 350 are maintained within the fluid flow. Because of the intermittent advancement of the input and outlet streams in a downstream direction along the adsorbent system, each zone must be defined by the points at which the various inlet and outlet streams are injected into, or withdrawn from, the continuous downstream fluid flow. Furthermore, as will be appreciated by one of ordinary skill in the art, the portions of the flowing fluid rich in each of the components (strongly-, intermediately-, and weakly-adsorbing compounds) will themselves be moving downstream as the inlet and outlet streams are advanced downstream, with respect to the stationary adsorbent chamber or chambers. Each zone, and the two inlet and three outlet streams, is described in greater detail below.

The first zone 310 is defined between the point of injection of the feed stream 311 (at the upstream end of the first zone 310) and the point of withdrawal of the raffinate stream 351 at the downstream end of the first zone 310. The feed stream 311 delivers a charge of weakly-, intermediately-, and strongly-adsorbing compounds to the fluid flow, which flows downstream through the first zone 310, countercurrent to the simulated upward flow of the solid adsorbent. At least a portion of each of the intermediately-adsorbing and the strongly-adsorbing compounds in the fluid flow are adsorbed within the pores of adsorbent, leaving the fluid flow depleted in intermediately-adsorbing and the strongly-adsorbing compounds at the bottom (downstream) end of the first zone 310 (i.e., a portion of the fluid flow rich in the weakly-adsorbing compound). (A very minor portion of the weakly-adsorbing compound may be adsorbed into the adsorbent at the point of injection of the feed stream 311 due to the displacing force of the incoming compounds carried into the system in the feed stream 311. However, any such weakly-adsorbing compounds will be relatively quickly displaced in the second zone 320, discussed in more detail below.) A raffinate withdrawal stream 351 removes a stream rich in the weakly-adsorbing compound from the fluid flow at the portion of fluid flow rich in the weakly-adsorbing compound. The raffinate withdrawal stream 351 will comprise primarily weakly-adsorbing compound(s), and it may also include desorbent from the fluid. In some embodiments, the raffinate will comprise weakly-adsorbing compound in an amount such that the molar ratio of weakly-adsorbing compound(s) to both intermediately- and strongly-adsorbing compound(s) in the raffinate is equal to or greater than any one of 10, 11, 12, 13, 14, 15, 20, 25, 30, 35, 40, 45, 50, 55, 60, 65, 70, 75, 80, 85, 90, 95, 100, 500, 1000, 10,000, and 100,000 to 1.

Ideally, the desorbent should be selected as a compound with different volatility from the components of the fluid mixture, such that simple distillation or other similar volatility-based separation process may separate the desorbent from each withdrawal stream. For instance, the raffinate withdrawn in stream 351 may be passed to a volatility-based separation system (e.g., one or more distillation columns), whereupon the weakly-adsorbing compound(s) may be relatively easily separated from any desorbent in the intermediate raffinate stream 351 (not shown in FIG. 3).

The second zone 320 is immediately upstream of the first zone 310, and is defined between the point of injection of the feed stream 311 and the point of withdrawal of the intermediate raffinate withdrawal stream 321. The third zone 330 is immediately upstream of the second zone 320, and is defined between the point of withdrawal of the intermediate raffinate withdrawal stream 321 and the point of withdrawal of the extract withdrawal stream 331. The processes occurring in both zones will be discussed together. At and just above (upstream from) the fresh feed injection 311, the solid adsorbent contains the quantity of intermediately- and strongly-adsorbing compounds that were adsorbed in the first zone 310, as well as any small amount of weakly-adsorbing compounds that may have been adsorbed at the point of injection of the feed stream 311, as previously noted. Although the strongly-adsorbing compounds will preferentially adsorb over the intermediately-adsorbing compounds, the pores of the adsorbent (with simulated upward flow relative to the input and output streams) should still contain a significant amount of adsorbed intermediately-adsorbing compound, at least by virtue of the adsorbent having just been contacted by the fluid flow comprising fresh feed from the fresh feed injection 311. On the other hand, any weakly-adsorbing compound(s) within the adsorbent will be quickly displaced by preferentially-adsorbing constituents of the fluid stream in the bottom portion of the second zone 320—in particular, any intermediately-adsorbing compound(s), strongly-adsorbing compound(s), or desorbent would readily displace the weakly-adsorbing compound(s), leaving the adsorbent holding substantially only strongly- and intermediately-adsorbing compounds (and possibly some desorbent) at least as of the middle portion of the second zone 320.

On the other hand, the portion of the fluid flow entering the top of the third zone 330, and flowing downstream toward the second zone 320, contains only strongly-adsorbing compound and desorbent. Due to the concentration differential between the flowing fluid and the adsorbent pores, as the adsorbent moves up (again, via simulated flow) through the second and third zones 320 and 330, the intermediately-adsorbing compound(s) are gradually displaced from the pores of the adsorbent by the preferentially adsorbed strongly-adsorbing compound and desorbent.

The displaced intermediately-adsorbing compound is thus kicked out into the downstream flowing fluid at some point in the lower portion of the third zone 330, such that it will flow some distance downstream in the flowing fluid, all the while passing over (simulated) counter-flowing solid adsorbent, which will include some empty pores and/or pores filled with weakly-adsorbing compound, which the intermediately-adsorbing compound will displace. As the adsorbed intermediately-adsorbing compound once more travels upstream, adsorbed in the simulated counter-flowing adsorbent, it will again eventually contact sufficient strongly-adsorbing compound (in the third zone 330) to displace it into the fluid stream. Thus it can be seen that an area of fluid in the adsorbent chamber 300 that is rich in the intermediately-adsorbing compound is created in the fluid flow at a point in the lower portion of the third zone 330 and upper portion of the second zone 320, giving the point at which the intermediate raffinate withdrawal stream 321 should be taken from the continuous downstream fluid flow in the adsorbent chamber 300, which point marks the boundary between the second and third zones 320 and 330.

The exact point at which the intermediate raffinate withdrawal stream 321 is withdrawn from the portion of the fluid flow that is rich in intermediately-adsorbing compound(s) will also in part be determined by the desired purity of the intermediate raffinate. Farther downstream, less of the intermediately-adsorbing compound will be present in the fluid flow (due, e.g., to the re-adsorption just described), but at such point there will be less of the strongly-adsorbing compound in the fluid, as well (due to more and more contact time with the adsorbent, such that a sufficient amount of the strongly-adsorbing compound has been adsorbed in the upstream-flowing adsorbent). Reference to "a sufficient amount" of strongly-adsorbing compound leaving the fluid stream is made herein because what amount is "sufficient" will depend upon the level of purity of the intermediately-adsorbing compound desired in the intermediate raffinate, which is a design choice for any ordinarily skilled artisan to make when implementing such aspects of the present invention. For high levels of purity, then a "sufficient amount" would of course be a high degree, perhaps substantially all, of the strongly-adsorbing compound, such that the strongly-adsorbing compound is present in the fluid flow in the chamber 300 in an amount less than or equal to any one of 5, 4, 3, 2, 1, 0.1, 0.01, or 0.001 wt % at the point of intermediate raffinate stream 321 withdrawal. Put another way, then, in such embodiments, the fluid flow is substantially free of strongly-adsorbing compound at the point of intermediate raffinate stream 321 withdrawal. For lower purity requirements, the strongly-adsorbing compound in other embodiments is present in the fluid flow in the adsorbent chamber 300 in amounts less than or equal to any one of 12, 11, 10, 9, 8, 7, or 6 wt % at the point of intermediate raffinate stream 321 withdrawal. Put in other terms, the intermediate raffinate should comprise intermediately-adsorbing compound such that the molar ratio of intermediately-adsorbing compound to both of the weakly-adsorbing and strongly-adsorbing compounds present in the intermediate raffinate should be at least any one of 10, 11, 12, 13, 14, 15, 20, 25, 30, 35, 40, 45, 50, 55, 60, 65, 70, 75, 80, 85, 90, 95, and 100 to 1, or more. In certain embodiments, the molar ratio of intermediately-adsorbing compound to both of the weakly-adsorbing and strongly-adsorbing compounds in the intermediate raffinate is at least 500 to 1, 1000 to 1, 1500 to 1, 2000 to 1, 5000 to 1, 10,000 to 1, 100,000 to 1, or 1,000,000 to 1.

The intermediate raffinate withdrawal stream 321 comprises the intermediately-adsorbing compound and desorbent (and, depending on purity requirements and placement of the stream as discussed above, possibly some strongly-adsorbing compound). As with the raffinate stream 351, the intermediate raffinate stream 321 is fed to a volatility-based separation system (e.g., a distillation column or the like) for relatively easy separation of the different-volatility desorbent from the intermediately-adsorbing compound(s).

According to the above, then, the second zone 320 may be described as an intermediately-adsorbing compound readsorption zone, and the third zone 330 may be described as an intermediately-adsorbing compound desorption zone.

The fourth zone 340 is defined at its downstream end by point of withdrawal of the extract withdrawal stream 331 from the fluid flow, and at its upstream end by the point of injection of the desorbent stream 341. The fluid flow at the downstream end of fourth zone 340 carries only strongly-adsorbing compound(s) and desorbent, whereas the fluid flow entering the upstream end of the fourth zone 340 consists of pure desorbent. As the desorbent stream 341 is carried into the fluid flow at the upstream end of the fourth zone 340, the fresh desorbent physically displaces a portion of the strongly-adsorbing compound from the desorbent by virtue of the rate of flow of the incoming stream 341. In addition, as the liquid flows downstream over the desorbent, the strongly-adsorbing compound in the pores of the counter-flowing adsorbent is further displaced by the desorbent due to the concentration differential. The fluid flow at the downstream end of the fourth zone 340 is therefore composed of both strongly-adsorbing compound(s) and desorbent. A portion of this liquid is withdrawn as the extract stream 331, while the remainder flows down into the third zone 330 as reflux. The extract stream 331, comprising strongly-adsorbing compound(s) and desorbent, may be passed to a separation system (e.g., one or more distillation columns or the like) for separation of the desorbent, in a similar manner to the previously-described withdrawal streams. The fourth zone 340 is therefore characterized as a strongly-adsorbing compound desorption zone. The extract may comprise strongly-adsorbing compound(s) in an amount such that the molar ratio of strongly-adsorbing compound(s) to both weakly- and intermediately-adsorbing compounds is equal to or greater than any one of 10, 11, 12, 13, 14, 15, 20, 25, 30, 35, 40, 45, 50, 55, 60, 65, 70, 75, 80, 85, 90, 95, and 100 to 1.

The fifth zone 350 serves as a buffer zone, segregating the depleted liquid of the downstream portion of the first zone 310 from the liquid to be drawn off as extract at the downstream end of the fourth zone 340. At the top of the fourth zone 340, the adsorbent pores are completely filled with desorbent. The fluid flow entering the top of the fifth zone 350 consists of the depleted liquid from the first zone 310 and desorbent. By properly regulating the flow rate into the fifth zone 350 (e.g., by controlling one or both of the desorbent stream 341 flow rate and the fluid flow from the fifth to the fourth zone), it is possible to prevent the flow of the depleted liquid into the fourth zone 340 and hence avoid contamination of the extract stream 331. For instance, sufficiently high flow rates of desorbent stream 341 may push the fluid comprising desorbent and strongly-adsorbing compound(s) downstream at a rate equal to or greater than the downstream flow rate of fluid at the bottom of the fifth zone 350, thereby keeping the portion of fluid flow rich in the strongly-adsorbing compound(s) in the lower portion of the fourth zone 340 ahead of (i.e., more downstream than) the downstream-flowing depleted liquid from the bottom of the first zone 310.

It should furthermore be noted that, the upstream-flowing (as simulated) adsorbent leaving the fourth zone 340 and passing through the fifth zone 350 comprises primarily desorbent adsorbed therein. Although the desorbent is preferentially adsorbed over the strongly- and intermediately-adsorbing compounds, such compounds will still displace the desorbent in the adsorbent as of the point of injection of the feed stream 311 so long as the feed stream 311 flow rate is sufficiently high to permit the incoming fluid to physically displace the adsorbed desorbent. (Suitable feed stream flow rates are discussed in more detail below.)

Although the five zones of FIG. 3 are shown as having differing relative lengths, such is illustrative only of certain example embodiments. Other embodiments may involve differing zone length (such as longer second zone 320 and shorter third zone 330), depending upon, e.g., the fluid flow rate, identity of mixture components, and desired purities. Yet other embodiments may include zones of equal length. It will be appreciated that the withdrawal points, i.e., where the "cuts" are made at the concentration distribution as discussed with respect to FIGS. 1 and 2, may be adjusted to achieve different purities by drawing fluid at different points from the concentration distribution established in the adsorbent chamber 300, as also discussed previously. For example, in general, the farther downstream the intermediate raffinate withdrawal 321 is placed, the more pure the intermediate raffinate will with respect to the intermediately-adsorbing compound (equating to shifting the cut on FIG. 1 to the left, as discussed previously). Thus, the zones of various embodiments may be of various different relative lengths.

As previously noted, the streams are periodically advanced together in a downstream direction (i.e., in the direction of fluid flow in the adsorption chamber or chambers), maintaining the sequence of injection and withdrawal streams cyclically through the adsorbent bed(s), thereby simulating counter-flow of the adsorbent in an upstream direction in the adsorbent chamber (illustrated by process line 315 in FIG. 3). Once a stream reaches the bottom of the adsorbent chamber 300, the next shift returns it to the top of the chamber, then the next shift moves that stream down the chamber once more, and so forth in a cyclical manner. Thus, the zones defined by the inlet and outlet streams would likewise be shifted downstream. For instance, referring again to FIG. 3, the next shift would move the first zone 310 to the top of the chamber 300, and each other zone would be shifted down one spot in the chamber 300. This periodic cyclical shifting effectively moves the above-defined zones continuously downstream relative to the stationary equipment (e.g., the adsorbent chamber 300), thereby simulating the countercurrent upstream "flow" of the stationary adsorbent beds disposed within that equipment. This shifting can, of course, be effected in a similar manner on a system comprising multiple adsorption chambers (such as the system depicted in FIG. 4). For instance, the shifting may be accomplished by utilizing a manifold arrangement. The valves in the manifold may be operated in a sequential manner to effect the shifting of the streams in the same direction as overall fluid flow throughout the adsorbent solids. In this regard see U.S. Pat. No. 3,706,812, which is incorporated herein by reference. Another means for producing a countercurrent flow in the solid adsorbent is a rotating disc valve by which the streams, e.g., feed, extract, desorbent, raffinate, and line flush, are advanced cyclically in the same direction through the adsorbent solids. Both U.S. Pat. Nos. 3,040,777 and 3,422,848, each of which is incorporated herein by reference, disclose suitable rotary valves. Both suitable manifold arrangements and disc valves are known in the art. More recently, a system has been described using dual rotary valves. See U.S. Pat. No. 8,168,845, also incorporated herein by reference.

Because the process is carried out cyclically as a continuous loop with respect to fluid flow within the adsorption chamber(s), the starting injection/withdrawal stream is arbitrary, but the sequence of the injection/withdrawal streams (and the sequence of the zones defined thereby) remains constant. For instance, the sequence of injections and withdrawals could be given as: feed injection-raffinate withdrawal-desorbent injection-extract withdrawal-intermediate raffinate withdrawal. However, it could just as well be given as: intermediate raffinate withdrawal-feed injection-raffinate withdrawal-desorbent injection-extract withdrawal.

In certain embodiments, any one of the feed or withdrawal streams could be consecutively duplicated, tripled, quadrupled, etc. In other words, although injection and withdrawal streams are frequently referenced herein in the singular, it will be understood that any one or more of the injection or withdrawal points in the above-noted sequence may comprise multiple of those injection or withdrawal points (e.g., the "feed injection" point in the aforementioned sequence may comprise two, three, four, or more feed streams), so long as the overall sequence of injection and withdrawal streams is maintained. Thus, with two fluid mixture feed injections, the sequence of injections and withdrawals would be given as: feed injection (1)-feed injection (2)-raffinate withdrawal-desorbent injection-extract withdrawal-intermediate raffinate withdrawal. Such configurations could, for instance, allow greater throughput or greater mixing (e.g., two injection points disposed on opposite sides of an adsorbent column), among other benefits, although at the cost of additional equipment.

Further, as previously noted, the adsorption system may comprise multiple adsorbent chambers 400 rather than a single adsorbent chamber 300, as is shown in FIG. 4. In FIG. 4, five columns in serial fluid communication (with recycle stream 415 to make the fluid flow therein cyclic) are depicted, one for each of the five zones 410, 420, 430, 440, and 450 therein, respectively corresponding to the five zones 310, 320, 330, 340, and 350 of FIG. 3. Similarly, the input and withdrawal streams of FIG. 4 (e.g., feed injection 411, intermediate raffinate withdrawal 421, extract withdrawal 431, desorbent injection 441, and raffinate withdrawal 451) correspond to the respective streams 311, 321, 331, 341, and 351 of FIG. 3, discussed above. Although FIG. 4 for convenience depicts a system comprising one adsorbent chamber 400 for each zone, more chambers may be used (e.g., such that a single zone could span multiple chambers), or fewer chambers could be used (e.g., such that a single chamber contains multiple zones and/or portions of zones). The periodic shifting of streams in a system according to the design of FIG. 4 would therefore be achieved by periodically shifting all injection and withdrawal streams together in a downstream direction (as shown in FIG. 4, to the right).

The system (whether single-chamber or multi-chamber) should be designed so as to ensure adsorption of the desired sufficient amount (see above discussion regarding the second and third zones) of the strongly-adsorbing compound as of the point of intermediate raffinate withdrawal 321. Further, the system advantageously is designed according to some embodiments such that both the intermediately- and strongly-adsorbing compounds have a net upstream flow with respect to the feed stream 311 injection point, thereby establishing a portion of the fluid flow concentrated in intermediately-adsorbing compound directly upstream of the feed injection point.

As illustrated in FIG. 3 and the above accompanying description, when the portion of the fluid flow concentrated in intermediately-adsorbing compound(s) is located directly upstream of the feed injection 311 point, and the weakly-adsorbing compound(s) have net downstream flow, the intermediate raffinate stream 321 may readily be substantially free of weakly-adsorbing compound(s) (where "substantially free" is defined in the same manner as above with respect to the strongly-adsorbing compound(s)), which may provide a significant advantage over designs wherein the intermediate withdrawal 321 point is located downstream of the feed (thereby having increased likelihood of weakly-adsorbing compound(s) being present). Put simply, establishing a net upstream flow of the intermediately-adsorbing compounds and a net downstream flow of the weakly-adsorbing compound(s) according to these embodiments may provide enhanced separation between the weakly-adsorbing and intermediately-adsorbing compounds. In combination with placing the intermediate raffinate withdrawal stream 321 at a point in the fluid flow wherein the strongly-adsorbing component(s) are substantially all adsorbed, such designs featuring directly upstream intermediate raffinate withdrawal enable withdrawal of an intermediate raffinate higher in purity of the intermediately-adsorbing compound relative to designs wherein intermediate raffinate is withdrawn immediately or nearly immediately downstream of the feed stream 311 injection point, in which case contamination of the intermediate raffinate with the weakly-adsorbing compound is more likely.

Design parameters to accomplish such an arrangement including intermediate raffinate withdrawal directly upstream of feed injection may include any one or more of: feed flow rate; desorbent flow rate; amount of adsorbent (either in the system as a whole, or on a per-area basis); pore volume and/or pore count in the adsorbent; and rate of simulated adsorbent counter-flow (in a SMB system, of course, the rate of simulated adsorbent counter-flow is established and adjusted via the frequency with which the injection and withdrawal streams are sequentially advanced to their next respective positions in the system, as described previously). For instance, in some embodiments, sufficient desorbent and/or pore space should be available to accommodate enough strongly-adsorbing compound(s) from the fluid flow to achieve any one or more of the above-described concentrations of strongly-adsorbing compound in the fluid stream in the second and third zones 320 and 330, according to various aspects, in addition to accommodating any desorbent adsorbed in the pores along with the strongly-adsorbing compound. Further, the fluid flow rate in the system may be controlled by regulation of the injection rate of the fluid mixture feed and the injection rate of the desorbent, further discussed below. The flow rate may further be controlled within an adsorbent chamber or chambers, e.g., by use of packing, trays, sieves, one-way valves and/or conduits within trays, and the like. Sufficient flow rates for the fluid mixture feed and desorbent can be selected by one of ordinary skill in the art with the benefit of this disclosure, so long as the resulting concentration distributions are achieved in accordance with the various embodiments described herein. Suitable flow rates for the fluid mixture feed, for instance, may fall within the range from a low of any one of about 2000, 2500, 3000, 3500, and 4000 gal/min to a high of any one of about 4000, 4500, 5000, 5500, 6000, 6500, 7000, 7500, and 8000 gal/min. Desorbent in some exemplary embodiments is introduced at a rate equal to any one of 0.8, 0.9, 1.0, 1.1, 1.2, 1.3, 1.4, 1.5, 1.6, 1.7, 1.8, 1.9, and 2.0 times the rate of fluid mixture feed.

In certain embodiments, control of the frequency of advancement of the injection and withdrawal streams is preferred, so as to establish a sufficiently high simulated counter-flow rate of the adsorbent so as to result in the above-discussed net upstream flow of strongly- and intermediately-adsorbing compounds. In particular, advancement in such embodiments should be of a higher frequency compared to conventional SMB systems, such as two, three, four, or in some embodiments five times the frequency of conventional advancement. For instance, where a conventional process may include advancing the feed and withdrawal streams once every minute, design according to such embodiments of the present invention may include advancing the feed and withdrawal streams once every 30 seconds. In some embodiments, the streams may be advanced once every 10, 15, 20, 25, 30, 35, 40, 45, 50, 55, 60, 65, 70, or 75 seconds. In certain embodiments, the frequency of advancement may be such that the streams are advanced once every $P_1$ to about once every $P_2$ seconds, where $P_1$ may be any one of 10, 15, 20, 25, 30, 35, 40, 45, and 50, and where $P_2$ may be any one of 15, 20, 25, 30, 35, 40, 45, 50, 55, 60, 65, 70, and 75. Thus, for example, the streams according to some embodiments may be advanced once every about 20 to about 40 seconds, or once every about 15 to about 50 seconds, and so on.

Further, it should be noted that an additional desorbent inlet stream could be added at some point in the third zone 330 between the intermediate raffinate withdrawal stream 321 and the extract withdrawal stream 331, theoretically to enhance the displacement of intermediately-adsorbing compound(s) from the adsorbent in the third zone. However, the design according to FIG. 3 (wherein the extract withdrawal stream 331 is directly upstream of the intermediate raffinate withdrawal stream 321, i.e., without an intervening desorbent injection stream) is preferred, because it takes advantage of the ability of the strongly-adsorbing compound(s) present in the flowing fluid to desorb any adsorbed intermediately-adsorbing compound(s) in the third zone 330 by displacing those compounds (simultaneously removing the strongly-adsorbing compounds from the fluid flow). This significantly reduces the complexity of the system and the cost as compared to a design that includes an additional desorbent stream between the intermediate raffinate withdrawal stream 321 and the extract withdrawal stream 331 (e.g., by eliminating the need to provide additional desorbent to the system, which would require more desorbent and/or greater loads on desorbent separations from the various withdrawal streams). Further, an additional desorbent stream would run the risk of displacing any strongly-adsorbing compounds in the adsorbent closer to the point of withdrawal of the intermediate raffinate withdrawal stream 321, thereby increasing the risk of contamination of the intermediate raffinate withdrawal stream 321 with strongly-adsorbing compound(s). Thus, in short, preferred designs include an extract withdrawal stream 331 directly upstream of the intermediate raffinate withdrawal stream 321; in addition to the intermediate raffinate withdrawal stream 321 being directly upstream of the feed stream 311.

Reduced Withdrawal Streams

Figure 5:
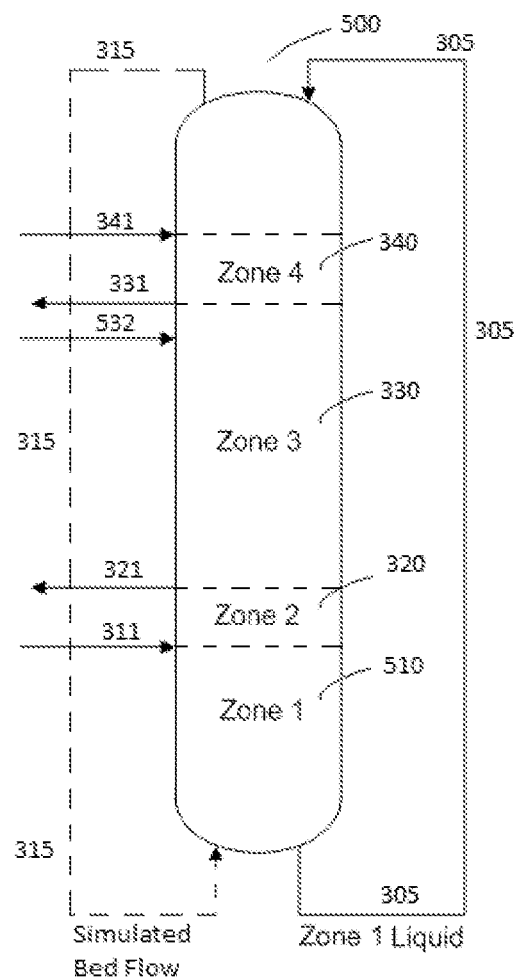
FIG. 5 is a schematic illustrating a continuous countercurrent flow adsorption process according to still further of the present invention.

In further aspects, the intermediately-adsorbing compound may be separated by means of forcing the weakly-adsorbing compound(s) into the withdrawal stream of the strongly-adsorbing compounds, which advantageously allows for use of a simplified system, as shown in FIG. 5. The modified adsorption system 500 and associated methods proceed in much the same manner as the systems and methods described above with respect to FIG. 3, but the raffinate withdrawal stream 351 is omitted. In such configurations, then, the fifth zone 350 of FIG. 3 is also omitted, and the altered first zone 510 is now defined at the upstream end by the point of injection of the feed stream 311, and at the downstream end by the point of injection of the desorbent stream 341. The weakly-adsorbing compound will therefore flow downstream from the first zone 310 to the fourth zone 340, whereupon it is joined by desorbent from the desorbent stream 341, which displaces adsorbed compounds (primarily strongly-adsorbing compound(s), along with some intermediately-adsorbing compound(s)) into the fluid. This fluid, comprising primarily strongly-adsorbing and weakly-adsorbing compound(s), and the desorbent, is withdrawn as the extract withdrawal stream 331. As with withdrawal streams of FIG. 3, this extract may be distilled (not shown) to separate the different-volatility desorbent, which may be returned to the adsorbent chamber 500 at return line 532 just downstream of the extract withdrawal stream 331. It can therefore be seen that this configuration allows use of one less distillation column where there is no need to separate the strongly- and weakly-adsorbing compounds from each other, thereby simplifying the overall separation where acceptable.

The liquid entering the top of the third zone 330 would therefore consist primarily only of desorbent, which would displace the intermediately-adsorbing compound in the adsorbent pores moving up through the third zone 330 from the second zone 230, similar to the displacement of the intermediately-adsorbing compound by the desorbent and strongly-adsorbing compound described above with respect to FIG. 3.

As with FIG. 3, the zones depicted in FIG. 5 may be of various different lengths in various embodiments, according to design needs as per the previous discussion. Furthermore, as with embodiments described with respect to FIG. 3, the starting injection/withdrawal stream is arbitrary, but the sequence of the injection/withdrawal streams (and the sequence of the zones defined thereby) according to these configurations remains constant. One difference from FIG. 3, however, lies in the definition of one zone boundary (e.g., the boundary between the third and fourth zones 330 and 340 as shown in FIG. 5), which constitutes the sequence of extract withdrawal and desorbent return, as no significant desorption or adsorption activity occurs within the adsorbent chamber(s) between these streams. For instance, then, the sequence of injections and withdrawals (listed as zone boundaries) could be given as: feed injection-desorbent injection-extract withdrawal/desorbent return-intermediate raffinate withdrawal. However, it could just as well be given as: intermediate raffinate withdrawal-feed injection-desorbent injection-extract withdrawal/desorbent return.

In alternative embodiments (not depicted in FIG. 5), similar advantages may be accomplished instead with an arrangement comprising 5 zones defined as in FIG. 3 (i.e., including both a raffinate and intermediate raffinate withdrawal stream), except that the raffinate withdrawal stream and extract stream may be combined into a single stream fed to a single distillation column for separation of the desorbent. This again simplifies the process, and may allow for significant energy savings as compared to systems including a distillation column (or other like separation unit) for each of the strongly- and weakly-adsorbing compounds.

Downstream Intermediate Raffinate Configurations

In yet other aspects, an intermediate raffinate withdrawal stream may be drawn off downstream from the feed injection stream, provided that the intermediate raffinate withdrawal stream is disposed along the adsorbent bed at a point immediately downstream from the desorbent injection point. In other words, such embodiments may involve an injection/withdrawal stream sequence of: feed-raffinate withdrawal-desorbent injection-intermediate raffinate withdrawal-extract. In such embodiments, sufficient amount of adsorbent and/or pore space in the adsorbent exists to completely adsorb the strongly- and weakly-adsorbing compounds in the feed stream, and the raffinate withdrawal point is sufficiently downstream of the feed injection point so as to allow complete or substantially complete adsorption of both the strongly- and intermediately-adsorbing compounds as of the point of raffinate withdrawal. ("Substantially complete" here means at least 99 wt % of each of the strongly-adsorbing and weakly-adsorbing compounds, by weight of each of the respective compounds in the feed stream.) Thus, the fluid flow at the raffinate withdrawal point of such embodiments is concentrated in the weakly-adsorbing compound(s), perhaps to the point of the substantial absence (i.e., 1 wt % or less each) of the intermediately- and strongly-adsorbing compounds.

Some such embodiments may therefore feature the withdrawal of the entire fluid flow, comprising the weakly-adsorbing compound(s), from the system, followed by downstream injection of the desorbent, which thereby establishes the concentration gradient between the two remaining classes of compounds in the system (intermediately- and strongly-adsorbing). In particular, the desorbent preferentially displaces the intermediately-adsorbing compound more quickly than it displaces the strongly-adsorbing compound, thereby establishing a point of concentration of the intermediately-adsorbing compound in the fluid flow upstream of the point at which the desorbent finally displaces the strongly-adsorbing compound. This enables one to take a "cut" of the intermediately-adsorbing compound at its point of concentration in the fluid flow.

The intermediate raffinate of such embodiments may have significant amounts of weakly-adsorbing compound(s) in addition to the intermediately-adsorbing compounds, and is therefore preferred in processes wherein purity requirements of the intermediately-adsorbing compounds are not as stringent (particularly as compared to purity requirements of the weakly- and/or strongly-adsorbing compounds).

As with other embodiments involving a single adsorbent chamber, embodiments including the just-described stream arrangements may be implemented in a multi-chamber system in certain aspects. Additionally, each respective zone may correspond to one chamber in certain aspects, or to more than one chamber in other aspects, or a combination thereof (i.e., some zones corresponding to multiple chambers, and some to respective single chambers).

Suitable Adsorbents, Desorbents, and Adsorption Conditions

Examples of adsorbents which may be used in any one or more of the present processes include non-zeolitic molecular sieves, such as carbon-based molecular sieves, and zeolitic molecular sieves, such as zeolites X and Y. For instance, X zeolites exchanged with barium or barium and potassium ions at their exchangeable sites, are known to be selective adsorbents for $C_8$ mixtures. Other suitable zeolitic molecular sieves are those having at least one pore system defined by a ten-membered ring of tetrahedrally coordinated atoms. Examples of suitable molecular sieves include those having a structure type selected from MFI, MEL, TON, MTT, MFS, MWW, FER, EUO, AEL, ITH, and AFO. In addition, suitable adsorbents may also include various metal-exchanged zeolites, particularly in embodiments involving separations of paraffin-olefin-aromatic/hetero-compound mixtures. Examples of suitable zeolites include faujasite (X, Y), beta, MCM-49, and the like. Potential metals exchanged onto the zeolites may include any one or more of Na, K, Mg, Ca, Sr, Ba, Cu, and other suitable metals for metal-exchanged zeolites. Suitable adsorbents in some embodiments may include metal-organic frameworks (MOFs) such as MOFs with open metal centers (e.g., CuBTC, MOF-74 series with various metal centers such as Co, Mn, Fe, Mg, Cu, and the like). In some embodiments the MOF is a zeolitic MOF (ZMOF), such as a ZMOF exchanged with one or more of various metal centers (e.g., Na, K, Mg, Ca, Sr, Ba, Cu, and any combination thereof).

Desorbents should be selected which displace or otherwise remove adsorbed compounds from the fluid mixture from the adsorbent. Preferably, the desorbent should have a different boiling point than any of the compounds of interest in the mixture (e.g., the weakly-adsorbing, intermediately-adsorbing, and/or strongly-adsorbing compounds) so as to allow for relatively easy separation of the desorbent from the mixture compounds, e.g., by distillation and/or fractional distillation, or the like. Suitable desorbents for $C_8$ separations, for example, may include benzene, toluene, and p-diethylbenzene (p-DEB), with p-DEB having become a commercial standard for $C_8$ separations. P-DEB is a "heavy" desorbent (higher boiling point than p-xylene from $C_8$ mixtures), which allows for easier recovery of the desorbent from the extract and raffinate streams by, e.g., fractional distillation. As another example, suitable desorbents for separating paraffin-olefin-aromatic/hetero-compound mixtures (e.g., for separating olefins as the intermediately-adsorbing compound from such mixtures) include any one or more of: higher olefins (e.g., nonene, decene); aromatics (e.g., p-DEB); and/or polar desorbents (e.g., methanol).

Adsorption conditions in general include a temperature range of from about 20° C. to about 250° C., with from about 60° C. to about 200° C. being preferred for para-xylene separation from $C_8$ mixtures, and about 50° C. to about 200° C. being preferred for olefin separation from paraffin-olefin-aromatic/hetero-compound mixtures, in certain embodiments. Adsorption conditions also include a pressure sufficient to maintain liquid phase, which may be from about atmospheric to 600 psig (100 to 4240 kPa). In some embodiments, pressure may depend in part upon vapor pressure of the starting fluid mixture feed. Desorption conditions generally include the same range of temperatures and pressure as used for adsorption.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention. Further, the term "comprising" is considered synonymous with the term "including" for purposes of Australian law. Likewise whenever a composition, an element or a group of elements is preceded with the transitional phrase "comprising," it is understood that we also contemplate the same composition or group of elements with transitional phrases "consisting essentially of," "consisting of," "selected from the group consisting of," or "is" preceding the recitation of the composition, element, or elements and vice versa. Furthermore, all patents, articles, and other documents specifically referenced are hereby incorporated by reference.

The invention claimed is:

1. A process for separating one or more compounds from a fluid mixture, the process comprising:
   (a) maintaining a continuous downstream fluid flow through an adsorbent system comprising an adsorbent in contact with the continuous downstream fluid flow;
   (b) providing to the continuous downstream fluid flow a feed stream comprising a fluid mixture comprising one or more weakly-adsorbing compounds, one or more intermediately-adsorbing compounds, and one or more strongly-adsorbing compounds, wherein the one or more strongly-adsorbing compounds comprise aromatics, hetero-compounds, or both; and further wherein the one or more weakly-adsorbing compounds comprise one or more paraffins;
   (c) providing a desorbent stream comprising a desorbent to the continuous downstream fluid flow;
   (d) withdrawing from the continuous downstream fluid flow a raffinate withdrawal stream rich in the one or more weakly-adsorbing compounds relative to the feed stream;
   (e) withdrawing from the continuous downstream fluid flow an intermediate raffinate withdrawal stream rich in the one or more intermediately-adsorbing compounds relative to the feed stream; and
   (f) withdrawing from the continuous downstream fluid flow an extract stream rich in the one or more strongly-adsorbing compounds relative to the feed stream;
   wherein the intermediate raffinate stream is withdrawn from the fluid flow directly upstream of the feed stream, and the extract stream is withdrawn from the fluid flow directly upstream of the intermediate raffinate stream.

2. The process of claim 1, further comprising maintaining a plurality of zones in the continuous downstream fluid flow, the plurality of zones comprising:
   a first zone defined at its upstream end by the point of injection of the feed stream to the continuous downstream fluid flow, and at its downstream end by the point of withdrawal of the raffinate withdrawal stream from the continuous downstream fluid flow;
   a second zone directly upstream of the first zone, said second zone defined at its upstream end by the point of withdrawal of the intermediate raffinate withdrawal stream from the continuous downstream fluid flow, and at its downstream end by the point of injection of the feed stream to the continuous downstream fluid flow;
   a third zone directly upstream of the second zone, said third zone defined at its upstream end by the point of withdrawal of the extract withdrawal stream from the continuous downstream fluid flow, and at its downstream end by the point of withdrawal of the intermediate raffinate withdrawal stream from the continuous downstream fluid flow;
   a fourth zone directly upstream of the third zone, said fourth zone defined at its upstream end by the point of injection of the desorbent stream to the continuous downstream fluid flow, and at its downstream end by point of withdrawal of the extract withdrawal stream from the continuous downstream fluid flow; and
   a fifth zone directly upstream of the fourth zone, said fifth zone defined at its upstream end by the point of withdrawal of the raffinate withdrawal stream from the continuous downstream fluid flow, and at its downstream end by the point of injection of the desorbent stream into the continuous downstream fluid flow.

3. The process of claim 2, further comprising periodically advancing each of the feed stream, the raffinate withdrawal stream, the desorbent stream, the extract withdrawal stream, and the intermediate raffinate withdrawal stream together along the continuous downstream fluid flow in a downstream direction so as to simulate flow of the adsorbent in a direction countercurrent with respect to the continuous downstream fluid flow.

4. The process of claim 3, wherein the adsorbent system comprises a single adsorbent chamber to which each of the feed stream and desorbent stream are provided, and from which each of the raffinate withdrawal stream, the extract withdrawal stream, and the intermediate raffinate withdrawal stream are withdrawn.

5. The process of claim 3, wherein the adsorbent system comprises multiple adsorbent chambers.

6. The process of claim 5, wherein:
each of the feed stream, the raffinate withdrawal stream, the desorbent stream, the extract withdrawal stream, and the intermediate raffinate withdrawal stream is provided to a first respective adsorbent chamber at a first point in time; and further
wherein the multiple adsorbent chambers are in cyclical serial fluid communication so as to enable the continuous downstream fluid flow to be established across all of the adsorbent chambers in the aggregate.

7. The process of claim 6, further comprising periodically advancing each of the feed injection stream, the raffinate withdrawal stream, the desorbent injection stream, the extract withdrawal stream, and the intermediate raffinate withdrawal stream together such that each stream is provided to a second respective adsorbent chamber at a second point in time, wherein each second respective adsorbent chamber is directly downstream of each first respective adsorbent chamber, with respect to the continuous downstream fluid flow across all of the adsorbent chambers.

8. The process of claim 3, wherein each stream is periodically advanced at a frequency of once every about 20 to about 40 seconds.

9. The process of claim 7, wherein each stream is periodically advanced at a frequency of once every about 20 to about 40 seconds.

10. The process of claim 9, wherein the intermediate raffinate further comprises desorbent, and further wherein the intermediate raffinate after withdrawal is provided to a volatility-based separation system to provide an effluent depleted in the desorbent relative to the intermediate raffinate.

11. The process of claim 10, wherein the one or more intermediately-adsorbing compounds comprise one or more olefins.

12. The process of claim 1, wherein the adsorbent comprises a metal-exchanged zeolite.

* * * * *